(12) United States Patent
Yu et al.

(10) Patent No.: US 6,586,012 B2
(45) Date of Patent: Jul. 1, 2003

(54) TASTE MASKED PHARMACEUTICAL LIQUID FORMULATIONS

(75) Inventors: Danny Yu, Somervile, NJ (US); Edward Roche, Paoli, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/253,683

(22) Filed: Sep. 24, 2002

(65) Prior Publication Data

US 2003/0064107 A1 Apr. 3, 2003

Related U.S. Application Data

(63) Continuation of application No. 09/598,157, filed on Jun. 21, 2000
(60) Provisional application No. 60/143,019, filed on Jul. 9, 1999, now abandoned.

(51) Int. Cl.$^7$ .............................. A61K 9/14; A61K 9/50
(52) U.S. Cl. ..................... 424/489; 424/494; 424/497
(58) Field of Search ................. 424/489, 441, 424/497, 464, 494; 514/772.4, 228.8, 230.2

(56) References Cited

U.S. PATENT DOCUMENTS

| | | | |
|---|---|---|---|
| 5,489,436 A | * | 2/1996 | Hoy et al. .................. 424/441 |
| 5,599,556 A | | 2/1997 | Meyer et al. |
| 5,614,222 A | * | 3/1997 | Kaplan ...................... 424/489 |
| 5,695,784 A | | 12/1997 | Pollinger et al. |
| 6,136,347 A | | 10/2000 | Pollinger et al. |

FOREIGN PATENT DOCUMENTS

| | | |
|---|---|---|
| EP | 0 470 687 A1 | 2/1992 |
| EP | 0 523 847 A1 | 1/1993 |
| EP | 0 551 820 A1 | 7/1993 |
| WO | WO 94/04505 A1 | 3/1994 |

OTHER PUBLICATIONS

Derwent Publications Ltd., London, GB; AN 1987–318176, XP002155620 & JP 62 226926 A (Teisan Seiyanky KK), Oct. 6, 1987, Abstract.
International Search Report Application No. PCT/US00/16969 dated Dec. 15, 2000.

* cited by examiner

Primary Examiner—James M. Spear
Assistant Examiner—Blessing Fubara

(57) ABSTRACT

A liquid composition for oral administration comprising a pharmaceutically active medicament coated with a taste masking effective amount of a polymer blend of (a) dimethylaminoethyl methacrylate and neutral methacrylic acid ester (MM/MAE) and (b) a cellulose ester, in an aqueous vehicle, wherein the polymer weight ratio of the cellulose ester to the MM/MAE is about 40:60 to about 90:10, preferably about 60:40. The liquid composition utilizes a "reverse enteric coating" which is soluble in the acid pH's of the stomach, generally about 1.0 to 4.0, but relatively insoluble at the non-acidic pH's of the mouth. The coatings provide for rapid release and absorption of the drug, which is generally desirable in the case of liquid dosage forms.

15 Claims, No Drawings

TASTE MASKED PHARMACEUTICAL LIQUID FORMULATIONS

CROSS REFERENCE TO RELATED APPLICATIONS

This application is a continuation of U.S. Ser. No. 09/598,157, filed Jun. 21, 2000 and claims the benefit of Provisional Application No. 60/143,019, filed Jul. 9, 1999, now abandoned.

FIELD OF THE INVENTION

This invention relates to oral pharmaceutical liquid formulations which effectively mask the unpleasant taste of pharmaceuticals or nutritional supplements with bitter or otherwise undesirable taste characteristics. More specifically, the invention relates to liquid suspensions of reverse enteric polymer coated dosage forms that mask the unpleasant taste of the active agent. The liquid suspensions may be swallowed without producing a bitter taste in the mouth, but the coated agent is immediately bioavailable upon exposure to the pH levels found in the stomach.

BACKGROUND OF THE INVENTION

Medicaments can be administered to the patient in many forms with oral administration being the most popular. Medicaments can be given to the patient orally as liquid solutions, emulsions, or suspensions, or in solid form such as capsules or tablets. Infants, children, older persons, and many other persons are unable to swallow whole tablets and capsules. Therefore, in cases where the dosage to be administered cannot be made into a very small tablet or capsule, it is desirable to provide the medicine in liquid or chewable form.

Many active ingredients, such as antibiotics, possess a strong, unpleasant taste. When a medicament is formulated as a tablet or capsule intended to be swallowed whole, the taste of the active ingredient is usually not an issue since the capsule keeps the active ingredient from contacting the mouth and the tablet can be coated to prevent contact of the active with the mouth for the short time the tablet is present in the mouth. In contrast, masking of the unpleasant taste characteristics of the active agent is an extremely important factor in the formulation of liquid and chewable pharmaceuticals. The palatability of the liquid or chewable dosage form is a critical factor in ensuring patient compliance.

In some cases, the unpleasant taste of the active medicament in a liquid or chewable formulation can be overpowered by adding flavoring ingredients and sweeteners to improve taste and palatability. However, where the active medicament possesses a particularly strong or bitter taste, such as is the case with many antibiotics, the mere addition of such flavoring ingredients and sweeteners is insufficient to improve taste and palatability. Accordingly, various taste masked coating compositions have been employed in the formulation of liquid suspension and chewable tablet dosage forms.

U.S. Pat. No. 5,599,556 discloses liquid formulations where the active ingredient is coated with a single outer polymeric coating derived from prolamine cereal grain proteins and a plasticizing agent. The coatings are designed to rapidly degrade once the composition leaves the mouth.

U.S. Pat. No. 5,489,436 discloses chewable tablets made from a coated medicament where the coating is a "reverse enteric coating" designed to be soluble at the lower pH of the stomach but relatively water insoluble at the higher pH's of the mouth. The coatings are comprised of a polymer blend of dimethylaminoethyl methacrylate and neutral methacrylic acid ester and a cellulose ester.

While the above mentioned reverse enteric coating method of taste masking oral formulations are disclosed in connection with chewable tablets, there is no disclosure of their use in a liquid formulation, where the taste masking coating will need to survive in an aqueous environment for an extended period. There is thus a need for a taste masking formulation suitable for an aqueous liquid suspension which is stable and retains its taste masking properties in the aqueous environment over an extended period, yet which exhibits immediate bioavailability after swallowing and ingestion.

SUMMARY OF THE INVENTION

The present invention provides a liquid composition for oral administration comprising a pharmaceutically active medicament coated with a taste masking effective amount of a polymer blend of (a) dimethylaminoethyl methacrylate and neutral methacrylic acid ester (MM/MAE) and (b) a cellulose ester, in an aqueous vehicle, wherein the polymer weight ratio of the cellulose ester to the MM/MAE is about 40:60 to about 90:10, preferably about 60:40. The liquid composition utilizes a "reverse enteric coating" which is soluble in the acid pH's of the stomach, generally about 1.0 to 4.0, but relatively insoluble at the non-acidic pH's of the mouth. The coatings provide for rapid release and absorption of the drug, which is generally desirable in the case of liquid dosage forms.

In preferred embodiments the active medicament useful in the taste masked liquid formulations of the present invention are antibiotic drugs, particularly levofloxacin, ofloxacin and related quinolone antibiotics, as well as other known antibiotics which have an unpleasant taste and are formulated for oral liquid administration like cephalosporins, macrolide antibiotics, penicillins and the like. Other active medicaments which may be beneficially employed in the liquid compositions of the invention include analgesic drugs, such as tramadol or codeine, anti-inflammatory drugs such as ibuprofen, naproxen and other NSAID's. Other active agents which for which the liquid compositions of the invention may be employed include gastro-intestinal drugs, antihistamines, decongestants, anti-depressants, anti-psychotics, antivirals, oncolytics, vaccines, antiepileptics (e.g. topiramate), anti-asthma compounds, antispasmodics, and the like.

In accordance with the invention, the particles of active medicament are generally spray coated with the polymer coating either directly or after granulation, and then the coated particles are admixed with other pharmaceutically acceptable additives such as sweeteners, flavorings and the like in an aqueous liquid vehicle for oral administration.

The invention also relates to a method of taste masking medicaments for oral liquid administration by utilizing the coating compositions of the invention.

DETAILED DESCRIPTION

The invention relates in particular to taste masked liquid preparations for oral administration comprising a pharmaceutically active medicament having an unpleasant taste which is coated with a reverse enteric coating. Reverse enteric coatings are those which are not water soluble at non-acidic pH's as are present in the mouth, but are soluble in the acid pH levels of the stomach. The coatings provide a protective layer which masks the unpleasant taste characteristics of the active ingredient in the mouth because of its low solubility therein but are readily soluble in the stomach and therefore provide immediate release of the active medicament in the stomach. The reverse enteric coatings encapsulate the active ingredient and thereby effectively and stably mask the taste of the active medicament.

In accordance with the invention, there is provided an orally consumable liquid composition comprising a pharmaceutically active agent in particle form contained in a liquid suspension having a pH greater than about 6.0, each particle comprising a core of pharmaceutically active agent, optionally associated with inactive pharmaceutical adjuvants; the core being coated with a taste masking effective amount of a polymer blend of (a) dimethylaminoethyl methacrylate and neutral methacrylic acid ester (MM/MAE) and (b) a cellulose ester, in an aqueous vehicle, wherein the polymer weight ratio of the cellulose ester to the MM/MAE is about 60:40 to about 70:30, preferably about 60:40. In a preferred embodiment, the formulation is prepared as a dry powder which is reconstituted with water to form the liquid compositions of the invention.

The details of the polymer blend used for the coatings and the coating techniques are described in U.S. Pat. No. 5,489,436, hereby incorporated by reference into the present application. In general, the cellulose acetate component, the solubility of which is pH independent, and the MM/MAE component, the solubility of which is pH dependent, are mixed in a ratio which provides the desired diffusion characteristics. The diffusion and solubility of the coating depends on the ratio of the two components and the physicochemical properties of the drug being coated. For the liquid formulations of the present invention, the inventors have found that the optimal ratio of CE:MM/MAE, particularly where the active agent is the quinolone antibiotic levofloxacin, is about 60:40 to 70:30, respectively. This ratio provides the desired diffusion characteristics, i.e. appropriate taste masking while present in the mouth but immediate disintegration and diffusion of the active agent when present at the acidic pH levels of the stomach. The diffusion characteristics thus obtained provides the appropriate immediate bioavailability of the active agent as is generally desirable in a liquid formulation.

If necessary, the particles of active agent are first granulated prior to coating, particularly if the particles are irregularly shaped and sized. Preferably, the particles to be coated will be in the range of about 3 to about 500 microns. The optimum thickness of the coating material applied to the particles will depend on the physicochemical characteristics of the active agent but is generally from about 40% to about 120% of applied film. The most preferred level of coating is between about 50% to about 120% by weight of coating to weight of the encapsulated active agent particles. For levofloxacin, the preferred coating level is from about 90% to about 120%, most preferably about 111% initial weight of the particles.

The ingredients for the polymer coating are as disclosed in U.S. Pat. No. 5,489,436. A variety of cellulose esters may be employed in the polymer coating. The preferred cellulose esters are cellulose acetate, cellulose acetate butyrate and cellulose triacetate, with cellulose acetate being most preferred. The preferred MM/MAE is the polymer blend sold under the tradename EUDRAGIT® E-100, available from Rohm Pharma. It is a copolymer based on dimethylaminoethyl methacrylates and neutral methacrylic acid esters with a mean molecular weight of 150,000. Other optional additives such as polyvinylpyrrolidone or 2 vinyl pyridine(V)/ styrene(S) copolymer may be added to the polymer blend coating.

The preparation of the formulation may be accomplished by a variety of coating techniques known in the art including fluidized bed coating, conventional top spray coating and wet granulation techniques. Preferably, fluidized bed coating with a Wurster column insert is used to apply the coating. In this procedure, the particles of active agent to be coated are suspended in an apparatus that creates an upward stream of air in which the particles move. The stream passes through an area of finely atomized coating material which causes the passing particles to be coated, after which the coated particles move upward through the Wurster column and then travel downward in a fluidized condition countercurrent to a flow of heated fluidized gas whereupon they are dried. The particles may reenter the upward stream for further coating.

Generally, the polymer coating material is dissolved in an organic solvent to make a solution for use in the fluidized bed coating process. A variety of organic solvents may be used, preferably acetone or an acetone methanol mix. The solvent is removed in the drying process and is thus not present in the final composition. The total polymer concentration in the coating solutions can vary, generally in the range of about 5 to about 20% by weight, preferably about 12% w/w.

Once the dried coated particles are obtained, the coated particles are admixed with other pharmaceutically acceptable adjuvants such as flavorings, sweeteners, thickening agents, colorings and the like to form the compositions of the invention for oral liquid administration. Suitable flavorants include fruit flavors, peppermint, licorice or bubble gum flavors. The sweetening agents may be for example bulk sweeteners such as sucrose or polyols (e.g. maltitol, sorbitol) and/or intense sweeteners such as saccharin, aspartame or acesulfame K. The preparation can be formed as a liquid, or as a powder for reconstitution with water by the pharmacist prior to dispensing.

It is also desirable to include an alkalizing agent in the aqueous liquid suspension to maintain the integrity of the reverse enteric taste masked coating. The alkalizing agents that are applicable for use in the present invention are those which are alkaline in aqueous solution and are capable of raising and maintaining the pH of the aqueous suspension above about 5. The alkalizing agent may be selected from any of the following compounds: alkali metal hydroxides, phosphates, carbonates and bicarbonates, such as sodium bicarbonate; magnesium hydroxide; magnesium oxide; magnesium phosphates; magnesium carbonate; magnesium hydroxide carbonate; magnesium glycinate; magnesium silicates; magnesium aluminum silicate; alkaline clays such as bentonite; zeolites; calcium oxide; calcium hydroxide; calcium phosphates; magaldrate; hydrotalcite; dihydroxyaluminum sodium carbonate; ammonium hydroxide; ammonium bicarbonate; ammonium carbonate; ethanolamine; diethanolamine; triethanolamine; tetrasodium ethylenediaminetetraacetic acid, its hydrates and the like. In the case of levofloxacin, sodium bicarbonate is preferred. One or more of such alkalizing agents may be used in an amount to raise the pH of the suspension above 5.0.

As stated, the taste masking formulations of the present invention satisfy the unique requirements of a liquid formulation. In accordance with the invention, there is provided a formulation which is stable, i.e. the taste masking properties survive in a "hostile" aqueous environment after reconstitution for at least the duration of the treatment period (in the case of antibiotics, 7–14 days), while still providing appropriate taste masking when the product is administered.

In order to further illustrate the present invention and the advantages thereof, the following specific examples are given, it being understood that these examples are intended only to be illustrations without serving as a limitation on the scope of the present invention.

EXAMPLE 1

Preparation of Taste Masked Levofloxacin Composition for Oral Liquid Administration To pharmaceutically active core particles of a coating solution of polymers as described below in Table 1 is prepared by adding the polymers to the acetone.

TABLE 1

Quantitative Composition of Coated Levofloxacin Beads

| Component | % w/w |
|---|---|
| Levofloxacin | 9.836 |
| Eudragit E100 | 4.328 |
| Cellulose Acetate, NF (CA 398-10) | 6.492 |
| Acetone, NF[a] | 79.344 |
| Total: | 100.0 |

[a]Acetone is removed during process and does not appear in the final product

The coating was performed in a Glatt GPCG-3 fluidized bed coater with a 7" Wurster Insert. The polymer weight ratio of Cellulose Acetate to Eudragit E100 in the taste mask coating for the two batches were 60:40 and 70:30 for batches 1 and 2, respectively. The actual coating level, calculated from potency assay, were 111% and 93% of initial respectively. The coating parameters and sieve analysis for the two batches are summarized in Tables 2 and 3.

TABLE 2

Coating Parameters of the Two Batches of Coated Levofloxacin Beads Manufactured using Glatt GPCG-3 coater with 7" Wurster

| Batch | Batch Size (kg) | Temperature During Spraying Inlet (° C.) | Temperature During Spraying Product (° C.) | Temperature During Spraying Exhaust (° C.) | Fluidization Air Flap (%) | Nozzle Size (mm) | Atomization Air (bar) | Partition Height (inch) | Spray Rate (g/min) | Spray Time (min) | Drying Time (min) | Product Drying Temp | Gross Yield (%) |
|---|---|---|---|---|---|---|---|---|---|---|---|---|---|
| 1 | 1.2 | 62–64 | 25–40 | 26–31 | 12 | 1.2 | 3 | 1 | 16.8–25.7 | 183 | 30 | 30–42° C. | 88.5 |
| 2 | 1.1 | 57–64 | 30–33 | 26–32 | 12 | 1.2 | 3 | 1 | 16.6–25.3 | 159 | 30 | 30–36° C. | 87.4 |

TABLE 3

Sieve Analysis of Coated Levofloxacin

| Mesh Size | Batch 1 (%) | Batch 2 (%) |
|---|---|---|
| >40 | 0.44 | 0.43 |
| 40–60 | 5.61 | 2.81 |
| 60–80 | 18.36 | 14.68 |
| 80–100 | 14.81 | 15.01 |
| 100–140 | 35.29 | 44.14 |
| 140–200 | 19.59 | 16.73 |
| <200 | 5.91 | 6.20 |
| Total | 100.0 | 100.0 |

Following coating of the levofloxacin particles, the coated particles are admixed with the adjuvants set forth in the following Table 4 to form a liquid composition for oral administration suitable for pediatric use.

TABLE 4

Quantitative Composition of Levofloxacin Powder for Reconstitution 125 and 250 mg/5 mL when reconstituted

| Component | g/5 mL | g/5 mL |
|---|---|---|
| Levofloxacin | 0.125[a] | 0.250[a] |
| Eudragit E100 | 0.05[a] | 0.10[a] |
| Cellulose Acetate, NF (CA 398-10) | 0.075[a] | 0.15[a] |
| Sodium Bicarbonate, USP | 0.02 | 0.02 |
| Microcrystalline Cellulose + Carboxymethyl Cellulose, NF (Avicel RC591) | 0.275 | 0.275 |
| Sucrose, NF (Baker's Special Granulated) | 2.5 | 2.5 |
| N&A Bubblegum Flavor | 0.001 | — |
| N&A Fruit Punch Flavor | — | 0.0075 |
| FD&C Red #40 | 0.00015 | 0.002 |
| Water qs ad | 5.0 mL[b] | 5.0 mL[b] |

[a]Based on theoretical coating level of 100% initial. Actual amount depends on the assay potency of the coated levofloxacin beads used in the batch.
[b]Water to be added by pharmacist before dispensing.

EXAMPLE 2

Dissolution Studies of Taste Masked Levofloxacin Composition for Oral Liquid Administration The reverse enteric coated levofloxacin particles, prepared as described in Example 1 were tested using a dissolution apparatus. Dissolution studies were conducted at pHs 1.2, 3 and 7.5 for the two batches of coated levofloxacin beads prepared as described in Example 1. The results, as summarized in Table 5, demonstrate that very little active agent is released at pH 7.5, while rapid release was observed at pH 1.2.

TABLE 5

Dissolution of Taste Masking Formulations

| Batch No. | Theoretical Coating (% initial) | Dosage Form | Dissolution Medium (900 mL) | pH | Dose/ Vessel (mg) | Percent Dissolved at | | | | | | |
|---|---|---|---|---|---|---|---|---|---|---|---|---|
| | | | | | | 10 min | 20 min | 30 min | 45 min | 60 min | 90 min | 120 min |
| 1 | 88 (111% actual) | Coated Levo Beads 250 mg levo equivalent | 0.1 N HCl 900 mL + 0.1% Tween 20 | 1.2 | 250 | 93.75 | 95.07 | 95.07 | 95.25 | 95.70 | 94.53 | 95.00 |
| 1 | 88 (111% actual | Coated Levo Beads 250 mg levo equivalent | 0.05 M KH2PO4/citric acid buffer 900 mL + 0.1% Tween 20 | 3.0 | 250 | 47.72 | 80.77 | 94.02 | 98.84 | 99.59 | 99.74 | 99.65 |
| 1 | 88 (111% actual) | Coated Levo Beads 250 mg levo equivalent | 0.05 M KH2PO4/ NaOH buffer 900 mL + 0.1% Tween 20 | 7.5 | 250 | 2.81 | 3.23 | 3.42 | 3.68 | 3.92 | 4.28 | 4.81 |
| 2 | 76 (93% actual) | Coated Levo Beads 250 mg levo equivalent | 0.1 N HCl 900 mL + 0.1% Tween 20 | 1.2 | 250 | 90.64 | 99.43 | 100.83 | 99.77 | 100.64 | 99.40 | 101.25 |
| 2 | 76 (93% actual) | Coated Levo Beads 250 mg levo equivalent | 0.05 M KH2PO4/citric acid buffer 900 mL + 0.1% Tween 20 | 3.0 | 250 | 18.66 | 27.32 | 35.38 | 46.98 | 56.94 | 75.98 | 89.01 |
| 2 | 76 (93% actual) | Coated Levo Beads 250 mg levo equivalent | 0.05 M KH2PO4/ NaOH buffer 900 mL + 0.1% Tween 20 | 7.5 | 250 | 3.22 | 3.71 | 4.06 | 4.81 | 5.30 | 6.20 | 7.08 |

Data for Information Only

We claim:

1. An orally consumable liquid composition comprising a pharmaceutically active agent in particle form contained in a liquid suspension having a pH greater than about 6.0, each particle comprising a core of pharmaceutically active agent, optionally associated with inactive pharmaceutical adjuvants; the core being coated with a taste masking effective amount of a polymer blend of (a) dimethylaminoethyl methacrylate and neutral methacrylic acid ester (MM/MAE) and (b) a cellulose ester, in an aqueous vehicle, wherein the polymer blend has a weight ratio of the cellulose ester to the MM/MAE of about 40:60 to about 90:10.

2. The orally consumable liquid composition of claim 1 wherein the coating on the particle is between about 40% to about 120% by weight of coating to weight of the encapsulated active agent particles.

3. The orally consumable liquid of claim 1 wherein the polymer blend has a weight ratio of the cellulose ester to the MM/MAE of about 60:40.

4. The orally consumable liquid of claim 1 wherein the cellulose ester is selected from cellulose acetate, cellulose acetate butyrate and cellulose triacetate.

5. The orally consumable liquid of claim 1 wherein the active agent is selected from antibiotic drugs, analgesic drugs, anti-inflammatory drugs, gastro-intestinal drugs, antihistamines, decongestants, anti-depressants, antipsychotics, antivirals, oncolytics, vaccines, antiepileptics, ant-asthma drugs, and antispasmodics.

6. The orally consumable liquid of claim 1 wherein the coated active agent particles are admixed with one or more pharmaceutically acceptable adjuvants.

7. The orally consumable liquid of claim 1 wherein the coated active agent particles are admixed with an alkalizing agent.

8. The orally consumable liquid composition of claim 6 wherein the cellulose ester is cellulose acetate and the ratio of the cellulose acetate to the MM/MAE is about 60:40 to about 70:30.

9. The orally consumable liquid of claim 1 wherein the polymer blend has a weight ratio of about 60/40.

10. The orally consumable liquid of claim 1 wherein the coating is from about 90% to about 120% of the initial weight of the particles.

11. The orally consumable liquid of claim 1 wherein the coating is 111% of the initial weight of the particles.

12. The orally consumable liquid of claim 1 wherein the coated particles are admixed with one or more pharmaceutically acceptable adjuvants.

13. The orally consumable liquid of claim 1 wherin the coated particles are admixed with an alkalizing agent.

14. The orally consumable liquid of claim 13 where the alkalizing agent is sodium bicarbonate.

15. The orally consumable liquid of claim 12 wherein the adjuvants are selected from flavorings, sweeteners, thickening agents, and colorings.

* * * * *